United States Patent
Burk et al.

(10) Patent No.: US 7,098,223 B2
(45) Date of Patent: Aug. 29, 2006

(54) ARYLSULFANYL AND HETEROARYLSULFANYL DERIVATIVES FOR TREATING PAIN

(75) Inventors: Robert M. Burk, Laguna Beach, CA (US); Sophie Beauchemin, Sherbrooke (CA)

(73) Assignee: Allergan, Inc., Irvine, CA (US)

( * ) Notice: Subject to any disclaimer, the term of this patent is extended or adjusted under 35 U.S.C. 154(b) by 127 days.

(21) Appl. No.: 10/938,792

(22) Filed: Sep. 10, 2004

(65) Prior Publication Data

US 2005/0032746 A1  Feb. 10, 2005

Related U.S. Application Data

(63) Continuation of application No. 10/232,264, filed on Aug. 29, 2002, now Pat. No. 6,825,221.

(60) Provisional application No. 60/346,844, filed on Oct. 18, 2001.

(51) Int. Cl.
| | |
|---|---|
| *A61K 31/44* | (2006.01) |
| *A61K 31/135* | (2006.01) |
| *C07D 401/00* | (2006.01) |
| *C07D 409/00* | (2006.01) |
| *C07C 321/00* | (2006.01) |

(52) U.S. Cl. ............... 514/332; 514/336; 514/646; 546/268.1; 546/280.4; 564/341

(58) Field of Classification Search ............... 546/310, 546/280.4, 268.1; 514/352, 332, 336, 646; 564/341
See application file for complete search history.

(56) References Cited

U.S. PATENT DOCUMENTS

| 5,811,459 A | 9/1998 | Breault et al. |
| 5,834,468 A | 11/1998 | Breault et al. |
| 5,843,942 A | 12/1998 | Breault et al. |
| 2001/0047008 A1 | 11/2001 | Baraldi et al. |

FOREIGN PATENT DOCUMENTS

EP  0037547  10/1981

(Continued)

OTHER PUBLICATIONS

Wallace, Mark, "Emerging drugs for neuropathic pain", Expert Opinion Emergin Drugs (2001) 6(2):249-259.*

(Continued)

*Primary Examiner*—Thomas McKenzie
*Assistant Examiner*—Binta Robinson
(74) *Attorney, Agent, or Firm*—Robert J. Baran; Martin A. Voet; Brent A. Johnson

(57) ABSTRACT

According to the invention there is provided a compound the formula I;

Figure 1:
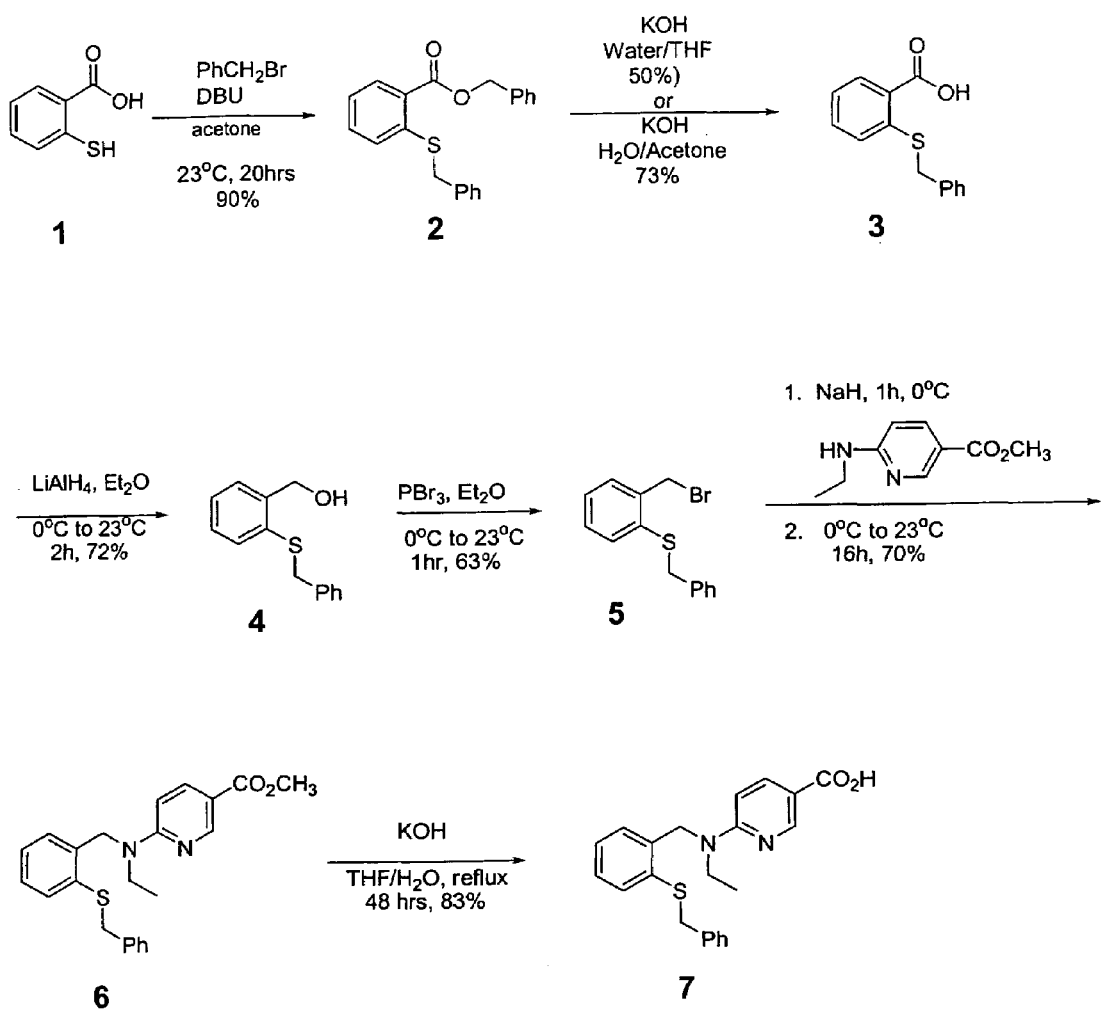

$$\begin{array}{c} R^3 \quad R^2 \\ | \quad\quad | \\ CH-N-B-R^1 \\ | \\ A \\ | \\ S-CH-X \\ | \\ R^4 \end{array}$$

wherein A, X, B, $R^1$, $R^2$, $R^3$ and $R^4$ are as defined in the specification.

23 Claims, 1 Drawing Sheet

FOREIGN PATENT DOCUMENTS

| | | |
|---|---|---|
| EP | 0218077 | 4/1987 |
| EP | 0351194 | 1/1990 |
| EP | 0375368 | 6/1990 |
| EP | 0381375 | 8/1990 |
| EP | 0385662 | 9/1990 |
| EP | 0385679 | 9/1990 |
| EP | 0375404 | 2/1994 |
| EP | 0375452 | 10/1994 |
| EP | 0385680 | 6/1995 |
| EP | 0385663 | 12/1995 |
| EP | 0752421 A | 1/1997 |
| WO | 9603380 A | 2/1996 |

OTHER PUBLICATIONS

Kennedy et al, "Studies on the Characterization of Prostanoid Receptors", Advances in Prostaglandin, Thromboxane and Leukotriene Research, 1983, vol. 11, 327-332.

* cited by examiner

ARYLSULFANYL AND HETEROARYLSULFANYL DERIVATIVES FOR TREATING PAIN

This application is a continuation of Ser. No. 10/232,264, filed Aug. 29, 2002 now U.S. Pat. No. 6,825,221, which application is based on, and claims the benefit of, U.S. Provisional Application No. 60/346,844, filed Oct. 18, 2001, and entitled ARYLSULFANYL AND HETEROARYLSULFANYL DERIVATIVES FOR TREATING PAIN, and which is incorporated herein by reference.

BACKGROUND OF THE INVENTION

1. Field of the Invention

This invention relates to novel, aromatic compounds and pharmaceutically-acceptable salts thereof which possess useful pharmacological properties. More particularly the compounds of the invention are antagonists of the pain enhancing effects of E-type prostaglandins. The invention also relates to processes for the manufacture of the aromatic compounds and pharmaceutically-acceptable salts thereof; to novel pharmaceutical compositions containing them; and to use of the compounds in pain relief.

2. Description of the Related Art

The compounds of the invention are useful in the treatment of pain such as the pain associated with joint conditions (such as rheumatoid arthritis and osteoarthritis), post-operative pain, post-partum pain, the pain associated with dental conditions (such as dental caries and gingivitis), the pain associated with burns (including sunburn), the treatment of bone disorders (such as osteoporosis, hypercalcaemia of malignancy and Paget's disease), the pain associated with sports injuries and sprains and all other painful conditions in which E-type prostaglandins wholly, or in part, play a pathophysiological role.

Non-steroidal anti-inflammatory drugs (NSAIDS) and opiates are the main classes of drugs in pain relief. However both possess undesirable side effects. NSAIDS are know to cause gastrointestinal irritation and opiates are known to be addictive.

Aromatic compounds which antagonize the pain-enhancing effects of E-type prostaglandins are disclosed in U.S. Pat. Nos. 5,811,459; 5,834,458 and 5,843,942. However, the need for compounds which relieve pain, without side effects, continues to exist.

BRIEF SUMMARY OF THE INVENTION

We have now found a class of compounds structurally different than NSAIDS and opiates, and useful in the relief of pain. The compounds of the invention may also possess antiinflammatory, anti-pyretic and anti-diarrheal properties and be effective in other conditions in which prostaglandin $E_2$ ($PGE_2$) wholly or in part plays a pathophysiological role.

According to the invention there is provided a compound the formula I;

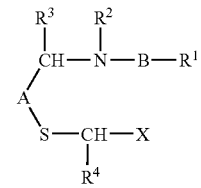

wherein:
A is an optionally substituted: phenyl, naphthyl, pyridyl, pyrazinyl, pyridazinyl, pyramidal, thienyl, thiazolyl, oxazolyl or thiadiazolyl;
B is an optionally substituted: phenyl, pyridyl, thiazolyl, oxazolyl, thienyl, thiadiazolyl, isoxazole, pyrazole, furyl, pyrrolyl, imidazolyl, pyrazinyl, pyridazinyl, pyrimidyl, pyridone, pyrimidone, pyrazinone or pyridazinone;
X is optionally substituted: pyridyl, pyrazinyl, pyrimidinyl, pyridazinyl, pyrrolyl, thienyl, furyl, imidazolyl, pyrazolyl, thiazolyl, isothiazolyl, oxazolyl, isoxazolyl or phenyl.
$R^1$ is $CO_2H$, $CO_2R$, $COSO_2NR_2$, tetrazolyl, P(O) or $(OR)_2$ or $SONH_2$
$R^2$ is H, $C_{1-6}$alkyl, $C_{2-6}$alkenyl, $C_{2-6}$alkynyl or $C_{1-3}$alkylaryl
$R^3$ is H or $C_{1-5}$alkyl
$R^4$ is H or $C_{1-5}$alkyl
Any of the above alkyl, alkenyl, alkynyl or aryl groups may optionally be substituted.

Particular substituents for ring carbon atoms in A and X include halo, trifluoromethyl, nitro, hydroxy, amino, $C_{1-4}$alkylamino, di$C_{1-4}$alkylamino, cyano, $C_{1-6}$alkoxy, —S(O)$_p$C$_{1-6}$alkyl (wherein p is 0, 1 or 2), $C_{1-6}$alkyl (optionally substituted by hydroxy, amino, halo, nitro or cyano), —S(O)$_p$CF$_3$ (wherein p is 0, 1 or 2), carbamoyl, $C_{1-4}$alkylcarbamoyl, di($C_{1-4}$alkyl)carbamoyl, $C_{2-6}$alkenyl, $C_{2-6}$alkynyl, $C_{2-4}$alkenylamino, N—$C_{2-4}$alkenyl-N—$C_{1-4}$alkylamino, di-$C_{2-4}$alkenylamino, S(O)$_p$C$_{2-6}$alkenyl (wherein p is 0, 1 or 2), $C_{2-4}$alkenylcarbamoyl, N—$C_{2-4}$alkenyl-N-alkylamino, di-$C_{2-4}$alkenylcarbamoyl, $C_{3-7}$cycloalkyl, $C_{3-7}$cycloalkylC$_{1-3}$alkyl, $C_{3-7}$cycloalkylC$_{2-3}$alkenyl, $C_{5-7}$cycloalkenyl, $C_{5-7}$cycloalkenyl C$_{1-3}$alkyl, $C_{5-7}$cycloalkenylC$_{2-3}$alkenyl, $C_{5-7}$cycloalkenylC$_{2-3}$alkynyl, $C_{1-4}$alkoxycarbonylamino, $C_{1-4}$ alkanoylamino, $C_{1-4}$alkanoyl(N—$C_{3-4}$alkyl)amino, $C_{1-4}$alkanesulphonamido, benzenesulphonamido, aminosulphonyl, $C_{1-4}$alkylaminosulphonyl, di($C_{1-4}$alkyl)aminosulphonyl, $C_{1-4}$alkoxycarbonyl, $C_{1-4}$alkanoyloxy, $C_{1-6}$alkanoyl, formylC$_{1-4}$alkyl, trifluoroC$_{1-3}$alkylsulphonyl, hydroxyimino $C_{1-6}$alkyl, $C_{1-4}$alkoxyiminoC$_{1-6}$alkyl $C_{1-6}$alkylcarbamoylamino, oxazoly, pyridyl, thiazolyl, pyrimidyl, pyrazinyl and pyridazinyl.

Where a ring nitrogen atom in A can be substituted without becoming quaternised, it is unsubstituted or substituted by $C_{1-4}$alkyl.

Particular substituents for ring carbon atoms in B include halo, amine, $C_{1-4}$alkylamino, di($C_{1-4}$alkyl)amino, trifluoromethyl, nitro, hydroxy, $C_{1-6}$alkoxy, $C_{1-6}$alkyl, cyano, —S(O)$_p$C$_{1-6}$alkyl (wherein p is 0, 1 or 2), carbamoyl, $C_{1-4}$alkylcarbamoyl and di($C_{1-4}$alkyl)carbamoyl.

Where a ring nitrogen atom in B can be substituted without becoming quaternised, it is unsubstituted or substituted by $C_{1-4}$alkyl.

Preferably A is phenyl, naphthyl, pyridyl, pyrazinyl, pyridazinyl, pyrimidyl, thienyl, thiazolyl, oxazolyl or thiadiazolyl.

More preferably A is phenyl, naphthyl, thiadiazolyl, thienyl, pyridyl or pyimidyl.

Most preferably A is phenyl or thienyl.

In particular A is phenyl.

Preferably B is pyridyl, phenyl, thiazolyl, thienyl, pyridazinyl, thiadiazolyl, imidazolyl, pyrazinyl, pyrimidyl, or oxazolyl.

More preferably B is pyridyl, phenyl, thiazolyl, thienyl, pyridazinyl or oxazolyl.

Yet more preferably B is pyridyl, phenyl, thienyl, pyridazinyl or thiazolyl.

Yet more preferably B is phenyl, pyridyl or pyridazinyl.

Most preferably B is pyridyl.

Preferably X is pyridyl, thienyl, thiazolyl, furyl or phenyl.

Most preferably X is phenyl.

Preferably $R^1$ is selected from the group consisting of $CO_2H$ and $CO_2R$, e.g. $CO_2H$.

Preferably $R^2$ is selected from the group consisting of H and $C_{1-6}$alkyl, e.g. $C_{1-6}$alkyl.

Preferably $R^3$ is H.

Preferably $R^4$ is H.

BRIEF DESCRIPTION OF THE DRAWING FIGURE

The FIGURE is a schematic of the chemical synthesis of 6-[(2-Benzylsulfanylbenzyl)ethyl amino]nicotinic acid, a preferred compound of the present invention. In the FIGURE, the numbers correspond to the numbering of the Examples.

DETAILED DESCRIPTION OF THE INVENTION

It is to be understood that, insofar as certain of the compounds of formula (I) defined above may exist in optically active or racemic forms, by virtue of the compounds of the formula (I) containing an asymmetric carbon atom, the invention includes in its definition of active ingredient any such optically active or racemic form which possesses pain relieving properties. The synthesis of optically active form may be carried out by standard techniques of organic chemistry well known in the art, for example by synthesis from optically active starting materials or by resolution of a racemic form. Similarly, pain relieving properties may be evaluated using the standard laboratory techniques referred to hereinafter.

As stated hereinbefore compounds of the formula (I) are antagonists of the pain enhancing effects of E-type prostaglandins and of value in the relief of pain which, for example, accompanies inflammatory conditions such as rheumatoid arthritis and osteoarthritis. Certain properties of the compounds may be demonstrated using the test procedures set out below:

(a) an in-vitro guinea pig ileum assay which assesses the inhibitory properties of a test compound against $PGE_2$-induced contractions of the ileum; ileum was immersed in oxygenated Krebs solution containing indomethacin (4 μ/ml) and atropine (1 μM) and which was maintained at 37° C.; the ileum was subject to a tension of 1 g; a control dose response curve for $PGE_2$-induced contraction of the ileum was obtained; test compound (dissolved in dimethylsulphoxide) was added to the Krebs solution and a dose response curve for the $PGE_2$-induced contraction of the ileum in the presence of the test compound was obtained; the $pA_2$ value for the test compound was calculated;

(b) an in-vitro assay in mice which assesses the inhibitory properties of a test compound against abdominal constriction response induced by the intraperitoneal administration of a noxious agent such as dilute acetic acid or phenylbenzoquinone (hereinafter PBQ) using the procedure disclosed in European Patent Application No. 0218077.

Prostaglandin receptors and in particular receptors for $PGE_2$ have been tentatively characterised by Kennedy et al. (Advances in Prostaglandin, Thromboxane and Leukotriene Research, 1982, 11, 327). The known $PGE_2$ antagonist SC-19220 blocks the effect of $PGE_2$ on some tissues such as guinea pig ileum or dog fundus but not on other tissues such as the cat trachea or chick ileum. Those tissues which did posses SC-19220 sensitive mediated effects were said to possess $EP_1$ receptors. Based on this compound of the present invention, possessing activity in Test (a), are $EP_1$ antagonists.

According to a further feature of the invention there is provided a pharmaceutical composition which comprises a compound of the formula (I) or an in-vivo hydrolysable ester thereof or an amide thereof, or a pharmaceutically-acceptable salt thereof, in association with a pharmaceutically-acceptable diluent or carrier.

The composition may be in a form suitable for oral use, suspension or emulsion; for topical use, for example a cream, ointment, gel, spray or aqueous or oily solution or suspension; for nasal use, for example a snuff, nasal spray or nasal drops; for vaginal or rectal use, for example a suppository or rectal spray; for administration by inhalation, for example as a finely divided powder or a liquid aerosol; for sub-lingual or buccal use, for example a table or capsule; or for parenteral use (including intravenous, subcutaneous, intramuscular, intravascular or infusion), for example a sterile aqueous or oil solution or suspension. In general the above compositions may be prepared in a conventional manner using conventional excipients.

The amount of active ingredient (that is a compound of the formula (I) or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition.

According to a further feature of the invention there is provided a compound of the formula (I) or an in-vivo hydrolysable ester or amide or a pharmaceutically-acceptable salt thereof, for use in a method of treatment of the animal (including human) body by therapy.

According to a further feature of the invention there is provided a method for the relief of pain in the animal (including human) body in need of such treatment which comprises administering to said body an effect amount of a compound of the formula I, or an in-vivo hydrolysable ester or amide or a pharmaceutically-acceptable salt thereof.

As mentioned above, a compound of the formula (I) is useful in treating the pain which, for example, accompanies inflammatory conditions such as rheumatoid arthritis and osteoarthritis. In using a compound of the formula I for therapeutic or prophylactic purposes it will generally be administered so that a daily dose in the range, for example, 0.1 mg to 75 mg per kg body weight is received, given if required in divided doses. In general lower doses will be administered when a parenteral route is employed. Thus, for example, for intravenous administration, a dose in the range, for example, 0.05 mg to 30 mg per kg body weight will generally be used. Similarly, for administration by inhalation, a dose in the range, for example, 0.05 mg to 25 mg per kg body weight will be used.

By virtue of their ability to relieve pain, the compounds of the formula I are of value in the treatment of certain inflammatory and non-inflammatory disease which are currently treated with a cyclooxygenase-inhibitory non-steroidal anti-inflammatory drug (NSAID) such as indomethacin, ketorolac, acetylsalicyclic acid, ibuprofen, sulindac, tolmetin and piroxicam. Co-administration of a compound of the formula I with a NSAID can result in a reduction of the quantity of the latter agent needed to produce a therapeutic effect. Thereby the likelihood of adverse side-effects from the NSAID such as gastrointestinal effects are reduced.

The compounds of the invention may also be used with other anti-inflammatory agents such as an inhibitor of the enzyme 5-lipoxygenase (such as those described in European Patent Applications Nos. 0351194, 0375368, 0375404, 0375452, 037547, 0381375, 0385662, 0385663, 0385679, 0385680.)

The compounds of the formula (I) may also be used in the treatment of conditions such as rheumatoid arthritis in combination with antiarthritic agents such as gold, methotrexate, steroids and penicillinamine, and in conditions such as osteoarthritis in combination with steroids.

The compounds of the present invention may also be administered in degenerative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

The compositions of the invention may in addition contain one or more other therapeutic or prophylactic agents known to be of value for the treatment of pain. Thus for example, a known opiate pain-killer (such as dextropropoxyphene, dehydrocodeine or codeine) or an antagonist of other pain or inflammation mediators, such as bradykinin, takykinin and calcitonin gene related peptides (CGRP), or an alpha$_2$adrenoceptor agonist, a GABA$_b$ receptor agonist, a calcium channel blocker, a sodium channel blocker, a CCK$_b$ receptor antagonist, a neurokinin antagonist or an antagonist and modulator of the action of glutamate at the NMDA receptor may usefully also be present in a pharmaceutical composition of the invention.

The compounds of the present invention may also be administered in bone diseases such as osteoporosis with calcitonin and bisphosphonates.

The invention is further illustrated by the following non-limiting Examples which are summarized in the reaction scheme of FIG. 1, wherein the compounds are identified by the same designator in the Examples and FIG. 1.

EXAMPLE 1

Thiosalicylic Acid (1)

Thiosalicylic acid was purchased from Aldrich Chemical Co., Inc., Milwaukee, Wis. 53233 USA.

EXAMPLE 2

2-Benzylsulfanyl Benzoic Acid Benzyl Ester (2)

A solution of thiosalicylic acid 1 (2.0 g, 13.0 mmol) in 13 mL of acetone was treated with 1,8-Diazabicyclo [5.4.0] undec-7-ene (7.8 mL, 52 mmol) and benzylbromide (6.2 mL, 52 mmol). The reaction was stirred at room temperature for 50 minutes. The mixture was concentrated under vacuum to remove the acetone. Water was added and the mixture was extracted with EtOAc (3X). The organic layer was washed with water, brine, dried over MgSO$_4$, filtered and concentrated in vacuo to give a yellow solid without purification.

EXAMPLE 3

2-Benzylsulfanyl Benzoic Acid (3)

To a suspension of 2-benzylsulfanyl benzoic acid benzyl ester 2 (113 mg, 0.34 mmol) was added 1.6 mL of 1N NaOH. KOH (1 pellet) was added and the reaction was continued overnight. The acetone was removed and a small amount of water was added. The aqueous solution was washed with CH$_2$Cl$_2$(3). The aqueous phase was acidified until pH of 2–3 was reached then extracted with CH$_2$Cl$_2$(3X), dried with MgSO$_4$ and filtered and concentrated to give a white solid.

EXAMPLE 4

(2-Benzylsulfanylphenyl)Methanol (4)

To a solution of 2-benzylsulfanyl benzoic acid 3 (50 mg, 0.206 mmol) in THF at 0° C. was added LiAlH$_4$ (0.62 mL of a 1.0 mL solution in THF, 0.62 mmol) and the mixture was stirred at 0° C. for 15 minutes then allowed to warm to room temperature. The solution was stirred for 2 hours. The mixture was cooled at 0° C. then methanol (MeOH) was added slowly followed by HCl (0.5N) and tetrahydrofuran (THF). The mixture was stirred at room temperature for 30 minutes. It was then concentrated to remove THF, extracted with CH$_2$Cl$_2$ (3X), dried over MgSO$_4$, filtered and concentrated to give 30 mg of the product as a yellow oil.

EXAMPLE 5

2-(2-Bromomethylphenylsulfanylmethyl)Benzene (5)

A solution of (2-Benzylsulfanyl)methanol 4 (120 mg, 0.522 mmol) in anhydrous Et$_2$O was cooled to 4° C. A solution of PBr$_3$ (49 µL, 0.52 mmol) in anhydrous Et$_2$O was added dropwise, keeping the temperature below 10° C. The reaction was allowed to warm to ambient temperature and stirred for one hour. The reaction was filtered through silica gel (2.0 g) and washed with Et$_2$O. The filtrate was washed with H$_2$O saturated aqueous sodium bicarbonate and brine. The organic layer was dried over Na$_2$SO$_4$, filtered and evaporated to give 95 mg of the named product as a yellow oil.

EXAMPLE 6

6-[(2-Benzylsulfanylbenzyl)ethylamino]Nicotinic Acid Methyl Ester (6)

A solution of methyl-6-ethylaminonicotinate in (59 mg, 0.332 mmol) DMF (0.8 mL) was added to sodium hydride (12 mg, 0.293 mL) in DMF (0.8 mL) at 0° C. The reaction was stirred for 1 hour and a solution of 2-(2-bromomethylphenyl sulfanylmethyl) benzene 5 (81 mg, 0.276 mmol) in 80 μL of DMF was added. The reaction was allowed to warm to ambient temperature and stirred for 18 hours. The solution was quenched with water and extracted with EtOAc (7X). The organic layers were combined, washed with water and brine twice, dried over $MgSO_4$ and evaporated to give a white solid that was recrystallized from EtOAc/hexane. The solid was purified with 5% EtOAc/hexane by chromatography to yield 350 mg (70%) of the named compound.

EXAMPLE 7

6-[(2-Benzylsulfanylbenzyl)ethylamino]Nicotinic Acid (7)

To a solution of the ester of Example 6 in THF (0.8 mL) was added a solution of KOH (14 mg, 0.255 mmol) in $H_2O$ (0.2 mL). The mixture was stirred at 50° C., then concentrated to remove THF. The aqueous phase was washed with ethyl ether, then the aqueous phase was acidified until pH 3–4 was reached. The acidified solution was extracted with $Et_2O$ or EtOAc (3X), dried over $MgSO_4$, filtered and concentrated in vacuo to give a white solid.

The compounds of Examples 6 and 7 represent the compounds of the present invention wherein A is phenyl, B is pyridyl and X is phenyl. The other compounds of the invention may be prepared by substituting the appropriate reactant(s) and carrying out the reactions illustrated in Examples 1 through 7 and Scheme 1 of the Drawing FIGURE. For example, the compounds of the present invention wherein B is phenyl may be prepared by use of methyl-6-ethylaminobenzoate for methyl-6-ethylamino nicotinate in the method of Example 6. In the compounds of the invention wherein A is pyridyl, 2-(2-Bromomethylpyridylsulfanylmethyl)benzene may be substituted for 2-(2-Bromomethylphenyl sulfanylmethyl)benzene (5) in the method of Example 6. In the compounds of the present invention wherein X is thienyl, 2-(2-Bromomethylphenylsulfanylmethyl)thiophene may be substituted for 2-(2-Bromomethylphenyl sulfanylmethyl)benzene (5) in the method of Example 6.

EXAMPLE 8

Alleviation of Chronic Pain

A model for chronic pain (in particular peripheral neuropathy such as causalgia) involves the surgical ligation of the L5 (and optionally the L6) spinal nerves on one side in experimental animals. Rats recovering from the surgery gain weight and display a level of general activity similar to that of normal rats. However, these rats develop abnormalities of the foot, wherein the hindpaw is moderately everted and the toes are held together. More importantly, the hindpaw on the side affected by the surgery appears to become sensitive to pain from low-threshold mechanical stimuli, such as that producing a faint sensation of touch in a human, within about 1 week following surgery. This sensitivity to normally non-painful touch is called "tactile allodynia" and lasts for at least two months. The response includes lifting the affected hindpaw to escape from the stimulus, licking the paw and holding it in the air for many seconds. None of these responses is normally seen in the control group.

Rats are anesthetized before surgery. The surgical site is shaved and prepared either with betadine or Novacaine. Incision is made from the thoracic vertebra Xlll down toward the sacrum. Muscle tissue is separated from the spinal vertebra (left side) at the L4–S2 levels. The L6 vertebra is located and the transverse process is carefully removed with a small rongeur to expose the L4–L6 spinal nerves. The L5 and L6 spinal nerves are isolated and tightly ligated with 6-0 silk thread. The same procedure is done on the right side as a control, except no ligation of the spinal nerves is performed.

A complete hemostasis is confirmed, then the wounds are sutured. A small amount of antibiotic ointment is applied to the incised area, and the rat is transferred to the recovery plastic cage under a regulated heat-temperature lamp. On the day of the experiment, at least seven days after the surgery, six rats per test group are administered the test drugs by intraperitoneal (i.p.) injection or oral gavage. For i.p. injection, the compounds are formulated in approximately 50% DMSO and given in a volume of 1 ml/kg body weight. The compound of Example 7 was tested at doses ranging between 30 and 3000 ng/kg. A volume equal to 1 ml/kg body weight of an appropriate concentration (ie. 1 mg/ml for a 1 mg/kg dose) of the compound of Example 7 formulated in approximately 50% DMSO was injected using an 18-gauge, 3-inch gavage needle that is slowly inserted through the esophagus into the stomach.

Tactile allodynia is measured prior to and 30 minutes after drug administration using von Frey hairs that are a series of fine hairs with incremental differences in stiffness. Rats are placed in a plastic cage with a wire mesh bottom and allowed to acclimate for approximately 30 minutes. The von Frey hairs are applied perpendicularly through the mesh to the mid-plantar region of the rats' hindpaw with sufficient force to cause slight buckling and held for 6–8 seconds. The applied force has been calculated to range from 0.41 to 15.1 grams. If the paw is sharply withdrawn, it is considered a positive response. A normal animal will not respond to stimuli in this range, but a surgically ligated paw will be withdrawn in response to a 1–2 gram hair. The 50% paw withdrawal threshold is determined using the method of Dixon, W. J., *Ann. Rev. Pharmacol. Toxicol.* 20:441–462 (1980). The post-drug threshold is compared to the pre-drug threshold and the percent reversal of tactile sensitivity is calculated based on a normal threshold of 15.1 grams. The compound of Example 7 was able to reduce the response to the tactile stimuli that indicate tactile allodynia. Compared to a saline solution, this compound reversed the allodynic pain by 25% at an i.p. dose of 100 ng/kg, 60% at 300 ng/kg, 90% at 100 mg/kg and 92% at 3000 ng/kg.

In comparison, when 6-[(2-Benzyloxy-5-bromobenzyl) ethylamino]nicotinic acid is tested in this pain model allodynic pain was reversed 10% at an i.p. dose of 30 ng/kg, 50% at 100 ng/kg, 55% at 300 ng/kg and 60% at ng/kg.

When the following compounds of the invention are substituted for 6-[(2-Benzylsulfanylbenzyl)ethylamino] nicotinic acid (7), in Example 8, it is believed that tactile sensitivity will be reduced:

6-[2-Benzylsulfanylbenzyl)ethylamino]benzoic acid or the methyl ester thereof.

6-[2-Pyridylsulfanylbenzyl)ethylamino]nicotinic acid or the methylester thereof.

6-[2-Benzylsulfanylthienylmethyl)ethylamino]nicotinic acid or the methylester thereof.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A compound of the formula I

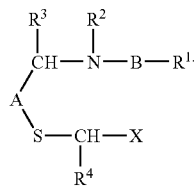

wherein A is an optionally substituted: pyridyl, pyrazinyl, pyridazinyl, pyramidal, thienyl, thiazolyl, oxazolyl or thiadiazolyl;

B is an optionally substituted: phenyl, pyridyl, thiazolyl, oxazolyl, thienyl, thiadiazolyl, isoxazole, pyrazole, furyl, pyrrolyl, imidazolyl, pyrazinyl, pyridazinyl, pyrimidyl, pyridone, pyrimidone, pyrazinone or pyridazinone;

X is selected from the group consisting of optionally substituted: pyridyl, pyrazinyl, pyrimidinyl, pyridazinyl, pyrrolyl, thienyl, furyl, imidazolyl, pyrazolyl, thiazolyl, isothlazolyl, oxazolyl, isoxazolyl and phenyl;

$R^1$ is selected from the group consisting of is $CO_2H$, $CO_2R$, $COSO_2NR_2$, tetrazolyl, $P(O)(OR)_2$ and $SONH_2$;

$R^2$ is selected from the group consisting of H, $C_{1-6}$alkyl, $C_{2-6}$alkenyl, $C_{2-6}$alkynyl and $C_{1-3}$alkylaryl;

$R^3$ is selected from the group consisting of H and $C_{1-6}$alkyl and $R^4$ Is selected from the group consisting of H and $C_{1-5}$alkyl.

2. The compound of claim 1 wherein A is selected from the group consisting of thiadiazolyl, thienyl, pyridyl and pyrimidyl.

3. The compound of claim 1 wherein A is selected from the group consisting of pyridyl and thienyl.

4. The compound of claim 1 wherein A is pyridyl.

5. The compound of claim 1 wherein B is selected from the group consisting of pyridyl, phenyl, thiazolyl, thienyl, pyridazinyl and oxazolyl.

6. The compound of claim 1 wherein B is selected from the group consisting of pyridyl, phenyl, thienyl, pyridazinyl and thiazolyl.

7. The compound of claim 1 wherein B is selected from the group consisting of phenyl, pyridyl and pyridazinyl.

8. The compound of claim 1 wherein B is phenyl.

9. The compound of claim 1 wherein X is selected from the group consisting of pyridyl, thienyl, thiazolyl, furyl and phenyl.

10. The compound of claim 1 wherein X is thienyl.

11. The compound of claim 1 wherein $R^1$ is selected from the group consisting of $CO_2H$ and $CO_2R$.

12. The compound of claim 1 wherein $R^1$ is COOH.

13. The compound of claim 1 wherein $R^2$ is selected from the group consisting of H and $C_{1-6}$alkyl.

14. The compound of claim 1 wherein $R^2$ is $C_{1-6}$alkyl.

15. The compound of claim 1 wherein $R^3$ is H.

16. The compound of claim 1 wherein $R^4$ is H.

17. The compound of claim 1 which is selected from the group consisting of
    6-[2-Benzylsulfanylbenzy)ethylamino]benzoic acid or the methyl ester thereof,
    6-[2-Pyridylsulfanylbenzyl)ethylamino]nicotinic acid or the methylester thereof and 6-[2-Benzylsulfanylthienylmethy)ethylamino]nicotinic acid or the methylester.

18. A pharmaceutical composition which comprises a compound according to claim 1 and a pharmaceutically-acceptable carrier.

19. A method for treatment of chronic pain in an animal in need of such treatment which comprises administering to said animal an effective amount of a compound according to claim 1.

20. The method of claim 19 wherein said chronic pain is peripheral neuropathy.

21. The method of claim 19 wherein said pain is the pain associated with the inflammatory conditions of rheumatoid arthritis or osteoarthritis.

22. The compound of claim 1 that is selected from the group consisting of 6-[2-Benzylsulfanylthienylmethyl)ethylamino]nicotinic acid and the methylester thereof.

23. The compound of claim 22 that is 6-[2-Benzylsulfanylthienylmethyl)ethylamino]nicotinic acid.

* * * * *